United States Patent
Tsujita

(10) Patent No.: US 7,324,211 B2
(45) Date of Patent: Jan. 29, 2008

(54) OPTICAL TOMOGRAPHIC IMAGE OBTAINING APPARATUS

(75) Inventor: Kazuhiro Tsujita, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 120 days.

(21) Appl. No.: 11/239,329

(22) Filed: Sep. 30, 2005

(65) Prior Publication Data

US 2006/0066865 A1    Mar. 30, 2006

(30) Foreign Application Priority Data

Sep. 30, 2004    (JP) .............................. 2004-285969

(51) Int. Cl.
*G01B 11/02* (2006.01)
*G01B 9/02* (2006.01)
(52) U.S. Cl. ...................... 356/497; 356/479
(58) Field of Classification Search ................ 356/477, 356/479, 497; 250/227.19, 227.27; 385/12
See application file for complete search history.

(56) References Cited

U.S. PATENT DOCUMENTS

| 6,008,898 | A  | * | 12/1999 | Furstenau et al. | ........... | 356/519 |
| 6,134,003 | A  | * | 10/2000 | Tearney et al. | ............. | 356/479 |
| 7,072,046 | B2 | * | 7/2006  | Xie et al. | .................... | 356/479 |
| 7,133,138 | B2 | * | 11/2006 | Horii et al. | ................... | 356/497 |
| 7,187,450 | B2 | * | 3/2007  | Drabarek | .................... | 356/497 |

FOREIGN PATENT DOCUMENTS

| JP | 2002-200037 A | 7/2002 |
| JP | 2003-199701 A | 7/2003 |

OTHER PUBLICATIONS

Andrew M. Rollins, et al., "Real-time in vivo imaging of human gastrointestinal ultrastructure by use of endoscopic optical coherence tomography with a novel efficient interferometer design", Optics Letters, vol. 24, No. 19, pp. 1358-1360, Oct. 1, 1999.

* cited by examiner

*Primary Examiner*—Michael A. Lyons
(74) *Attorney, Agent, or Firm*—Sughrue Mion, PLLC

(57) ABSTRACT

An optical tomographic image obtaining apparatus, capable of obtaining optical tomographic images at high resolution, is miniaturized. During obtainment of an optical tomographic image, a mirror rotating section rotates a mirror, to rotate the irradiation direction of a measuring light beam. Operations of an optical path length changing section are controlled such that a measurement point along the optical path direction is moved for every rotation of the irradiation direction. A sheath rotating section rotates a sheath to move the position of a lens fixed within a lens holder by a threaded mechanism, to move the focusing position of the measuring light beam in the optical path direction, to match the position of the measurement point. Therefore, the movement speed of the focusing position can be reduced compared to conventional apparatuses. Accordingly, the necessity of a large focusing position moving means, which is capable of high speed movement, is obviated.

15 Claims, 4 Drawing Sheets

OPTICAL TOMOGRAPHIC IMAGE OBTAINING APPARATUS

This application claims priority to Japanese Patent Application No. JP 2004-285969, filed on Sep. 30, 2004.

BACKGROUND OF THE INVENTION

1. Field of the Invention

The present invention relates to an optical tomographic image obtaining apparatus that obtains optical tomographic images of targets of measurement, by irradiating the targets of measurement with measuring light beams, and employing interference between the measuring light beams, which are reflected at predetermined depths of the irradiated portions, and reference light beams. Particularly, the present invention relates to an optical tomographic image obtaining apparatus that comprises a focusing position moving means, for moving the focusing position of the measuring light beam.

2. Description of the Related Art

Development of optical tomographic image obtaining apparatuses, for obtaining optical tomographic images of living organisms and the like, is progressing. As the method of obtaining optical tomographic images, there are methods that employ optical interference by coherent light beams, to which frequency sweeping has been administered, and methods that employ optical interference by low coherence light beams.

OCT (Optical Coherence Tomography) apparatuses that obtain optical tomographic images, by measuring light intensities of low coherence coherent light beams with heterodyne demodulation are being put into practical use.

An OCT apparatus divides a low coherence light beam, emitted from a light source, such as an SLD (Super Luminescent Diode) into a measuring light beam and a reference light beam. The frequency of either the measuring light beam or the reference light beam is shifted by a piezoelectric element or the like. The measuring light beam is irradiated onto a target of measurement. The measuring light beam which is reflected from the irradiated portion and the reference light beam are caused to interfere, and the light intensity of the coherent light beam resulting from the interference is measured by heterodyne demodulation, to obtain optical tomographic data. Data regarding a predetermined depth of the irradiated portion (hereinafter, referred to as "measurement point"), at which the optical path lengths of the reference light and the measuring light are matched, is obtained by slightly moving mirrors provided along the optical path of the reference light beam, thereby slightly changing the optical path length of the reference light beam. Alternatively, optical tomographic images of predetermined regions may be obtained by repeating measurements while slightly shifting the position, onto which the measuring light is irradiated (as disclosed in "Real-time in vivo imaging of human gastrointestinal ultrastructure by use of endoscopic optical coherence tomography with a novel efficient interferometer design" by Andrew M. Rollins and Rujchai Ungarunyawee, OPTICS LETTERS, Vol. 24, No. 19, pp. 1358-1360, Oct. 1, 1999).

By utilizing such an OCT apparatus, it is possible to diagnose the degree of penetration in early stages of cancer and the like. Therefore, methods for obtaining optical tomographic images from within body cavities by guiding measuring light beams and reflected measuring light beams with OCT probes, which are insertable into forceps channels of endoscopes, are being developed (as disclosed in Japanese Unexamined Patent Publication No. 2002-200037). Japanese Unexamined Patent Publication No. 2002-200037 discloses an OCT apparatus comprising an OCT probe, constituted by: an optical fiber, for guiding a measuring light beam; and a mirror, for reflecting the measuring light beam 90°, provided at the distal end of the optical fiber. The OCT probe is inserted into a body cavity via a forceps channel of an endoscope, and optical tomographic images of the walls of the body cavity are displayed by rotating the mirror at the distal end of the optical fiber.

Recently, resolution of images is becoming higher, due to improvements in light sources and the like, which are employed in OCT apparatuses. Resolution in the direction along the optical axis of a measuring light beam, that is, in the depth direction, has improved to the order of several microns. Meanwhile, it is necessary to decrease the beam diameter of the measuring light beam at the measurement point, in order to improve resolution in the direction perpendicular to the optical axis (hereinafter, referred to as "horizontal resolution"). An objective lens system having a great numerical aperture is required to decrease the beam diameter at the measurement point. However, in the case that an objective lens system having a great numerical aperture is employed, the focal depth becomes shallow. Accordingly, if the position of the measurement point in the direction of the optical axis shifts even slightly from the focal point, the horizontal resolution deteriorates conspicuously. For this reason, ACT apparatuses that have functions of moving the focal point positions of objective lens systems have been proposed (as disclosed in Japanese Unexamined Patent Publication No. 2003-199701).

In the optical tomographic image obtaining apparatus disclosed in Japanese Unexamined Patent Publication No. 2003-199701, a measuring light beam is irradiated onto a point of a target of measurement. The measurement point is moved along the direction of the optical axis at the irradiated portion, to obtain tomographic data up to a desired depth. When measurements are completed at that point, the irradiation position of the measuring light beam is moved slightly in a direction substantially perpendicular to the optical axis direction, and tomographic data is obtained up to a desired depth in a similar manner. These operations are repeated while slightly moving the irradiation position of the measuring light beam, to obtain optical tomographic images. Accordingly, it is necessary to move the focusing position of the measuring light beam to match the movement of the measurement point in the optical axis direction. Movement of the measurement point in the optical axis direction is performed at extremely high speed. Therefore, it is necessary for the movement of the focusing position of the measuring light beam to be performed at extremely high speed. However, a large and complex focusing position moving means is necessary in order to move the focusing position of the measuring light beam at high speed. This leads to a problem that optical tomographic image obtaining apparatuses become large and complex.

SUMMARY OF THE INVENTION

The present invention has been developed in view of the above circumstances. It is an object of the present invention to provide a miniature optical tomographic image obtaining apparatus, which is capable of obtaining optical tomographic images at high resolution.

The present invention provides an optical tomographic image obtaining apparatus that divides a low coherent light beam, having a coherence length of 20 µm or less, into a measuring light beam and a reference light beam; changes the optical path length of at least one of the reference light beam and the measuring light beam; irradiates the measuring light beam onto a target of measurement; receives the measuring light beam, which is reflected from the target of measurement; causes the reflected measuring light beam and the reference light beam to interfere; and measures the light intensity of the coherent light after the interference, to obtain optical tomographic images of the target of measurement, comprising:

irradiation direction rotating means, for causing the irradiation direction of the measuring light beam to rotate about a single point;

optical path length changing means, for changing the optical path length of at least one of the reference light beam and the measuring light beam, synchronous with the rotation of the irradiation direction of the measuring light beam;

an objective lens system, for focusing the measuring light beam; and focusing position moving means, for moving the focusing position in the direction of the optical axis of the measuring light beam, by moving the focal point of the objective lens system, synchronous with the rotation of the irradiation direction of the measuring light beam.

Note that here, "receives the measuring light beam, which is reflected from the target of measurement" refers to receiving light, which is dispersed at the surface or the interior of the target of measurement, in addition to light, which is reflected at the surface or the interior of the target of measurement.

In addition, "causing the irradiation direction of the measuring light beam to rotate about a single point" refers to either continuous unidirectional rotation, or reciprocal rotation within a predetermined angular range.

Further, "moving the focal point of the objective lens system, synchronous with the rotation of the irradiation direction of the measuring light beam" refers to either moving the focal point at every single rotation of the irradiation direction of the measuring light beam, or moving the focal point for every predetermined number of rotations. Alternatively, the focal point may be moved continuously, synchronous with the rotation. Note the optical path length changing means changes "the optical path length of at least one of the reference light beam and the measuring light beam, synchronous with the rotation of the irradiation direction of the measuring light beam". Thereby, the measurement point within the target of measurement, along the optical axis direction of the measuring light beam, is changed. Accordingly, the focusing point moving means moves the focal point of the objective lens system such that the focusing position of the measuring light beam is in the vicinity of the measurement point.

If the irradiation direction rotating means rotates the irradiation direction of the measuring light beam unidirectionally; and the optical path length changing means continuously changes the optical path length, synchronous with the rotation; then the focusing position moving means may continually move the focusing position, synchronous with the rotation.

The irradiation direction rotating means, the objective lens system, and the focusing position moving means may be provided at the distal end of a probe, which is insertable into a forceps channel of an endoscope.

If the target of measurement is a portion of a living organism, then the wavelength of the low coherent light beam may be within a range of 600 nm to 1700 nm.

The optical tomographic image obtaining apparatus according to the present invention divides a low coherent light beam, having a coherence length of 20 µm or less, into a measuring light beam and a reference light beam; changes the optical path length of at least one of the reference light beam and the measuring light beam; irradiates the measuring light beam onto a target of measurement; receives the measuring light beam, which is reflected from the target of measurement; causes the reflected measuring light beam and the reference light beam to interfere; and measures the light intensity of the coherent light after the interference, to obtain optical tomographic images of the target of measurement, and comprises: irradiation direction rotating means, for causing the irradiation direction of the measuring light beam to rotate about a single point; optical path length changing means, for changing the optical path length of at least one of the reference light beam and the measuring light beam, synchronous with the rotation of the irradiation direction of the measuring light beam; an objective lens system, for focusing the measuring light beam; and focusing position moving means, for moving the focusing position in the direction of the optical axis of the measuring light beam, by moving the focal point of the objective lens system, synchronous with the rotation of the irradiation direction of the measuring light beam. Therefore, the movement speed of the focal point of the objective lens system is reduced, compared to conventional apparatuses. Accordingly, the necessity of the conventional large focusing position moving means, which is capable of high speed movement, is obviated, and a miniature optical tomographic image obtaining apparatus capable of obtaining optical tomographic images at high resolution can be provided.

If the irradiation direction rotating means rotates the irradiation direction of the measuring light beam unidirectionally; and the optical path length changing means continuously changes the optical path length, synchronous with the rotation; then the focusing position moving means may continually move the focusing position, synchronous with the rotation. In this case, tomographic data can be obtained from measurement points, which are arranged in a spiral. In addition, it becomes unnecessary to move the focal point in a stepwise manner with each rotation of the irradiation direction. Therefore, a focusing position moving means having a simple construction may be employed. Accordingly, a further miniaturized optical tomographic image obtaining apparatus capable of obtaining optical tomographic images at high resolution can be provided.

Optical tomographic image obtaining apparatuses are effective for inspections of living tissue, and there are cases that they are built into endoscopes and utilized. In such cases, the irradiation direction rotating means, the objective lens system, and the focusing position moving means are provided at the distal end of a probe, which is insertable into a forceps channel of an endoscope. It is extremely difficult to mount these means of conventional apparatuses into such a small space. However, if the construction of the apparatus is that of the present invention, these means can easily be provided within the probe.

If the target of measurement is a portion of a living organism, then the wavelength of the low coherent light beam may be within a range of 600 nm to 1700 nm. In this case, transmittance with respect to living tissue is high, and reliable optical tomographic images can be obtained.

DESCRIPTION OF THE PREFERRED EMBODIMENTS

Figure 1:
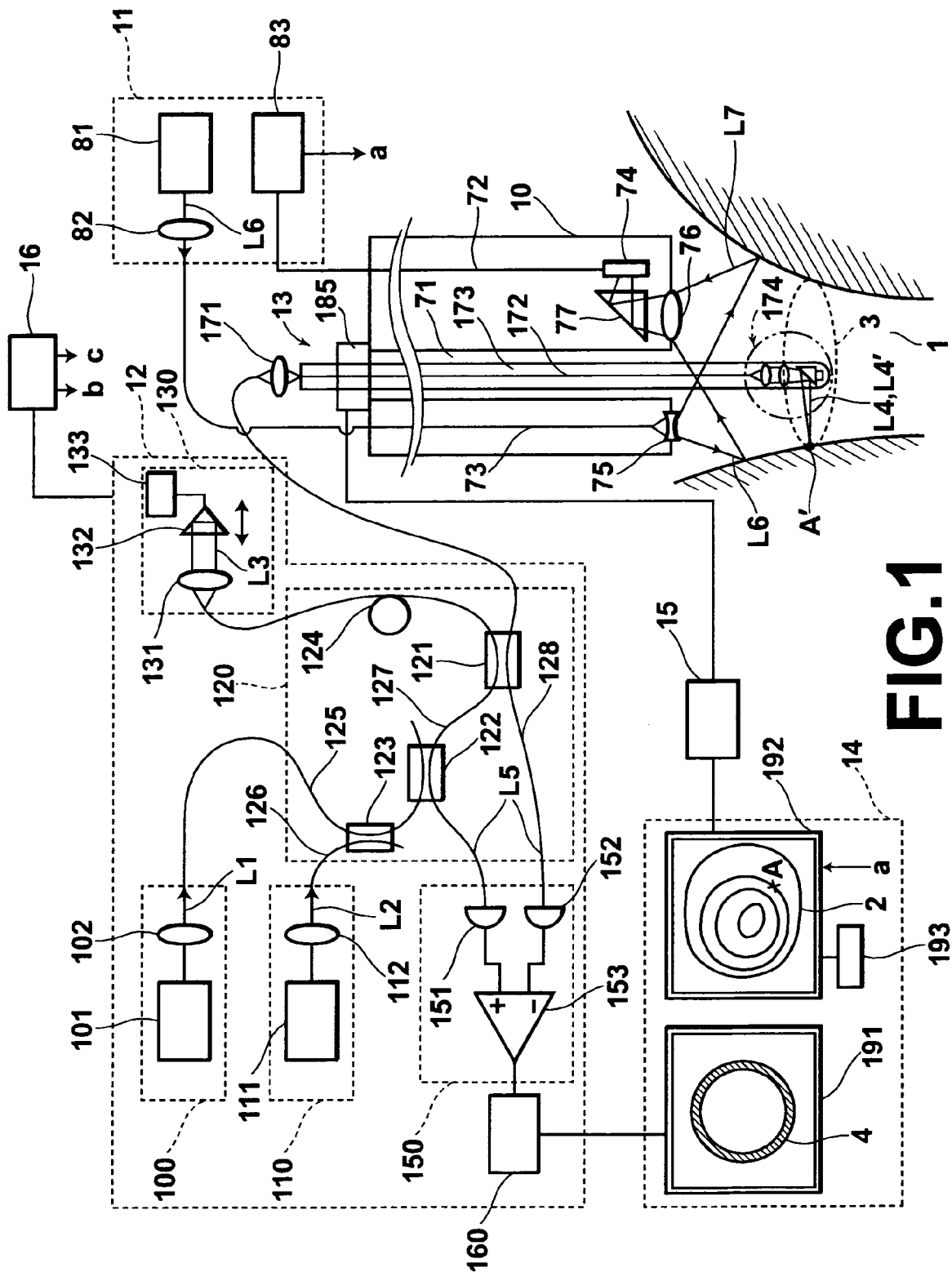
FIG. 1 is a schematic view illustrating the entire construction of an optical tomographic image obtaining system according to a first embodiment of the present invention.
Figure 2:
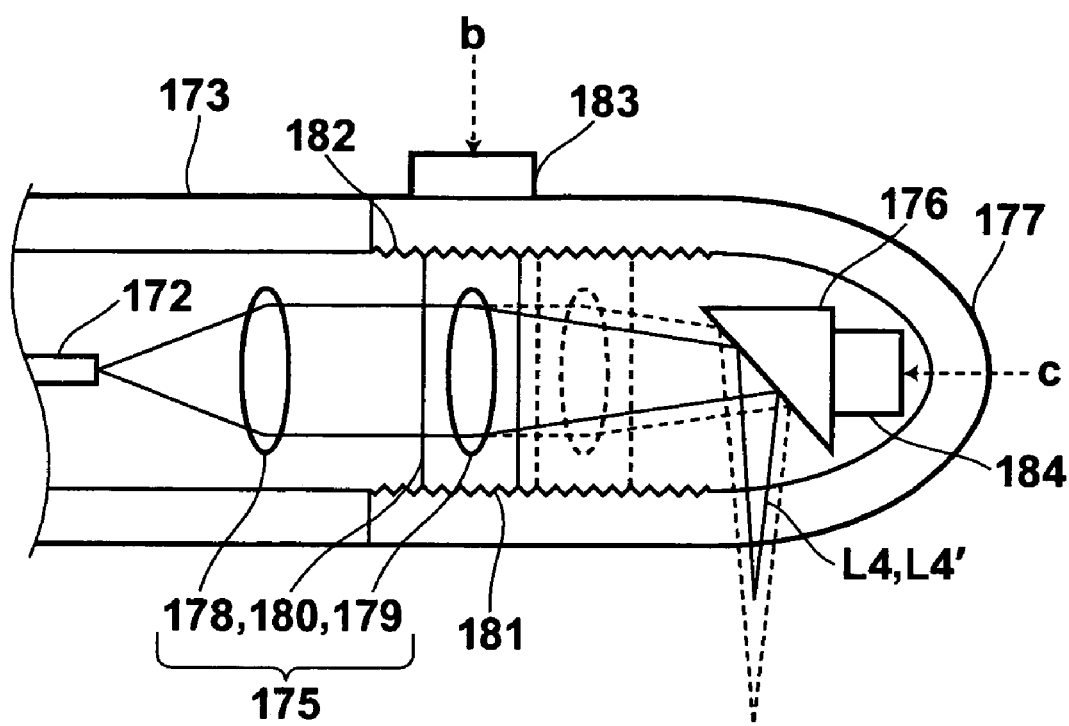
FIG. 2 is a magnified schematic view of an irradiating/light receiving section of the optical tomographic image obtaining system of FIG. 1.

Hereinafter, preferred embodiments of the present invention will be described with reference to the attached drawings. First, an optical tomographic image obtaining system according to a first embodiment of the present invention will be described with reference to FIG. 1 and FIG. 2. FIG. 1 is a schematic view illustrating the entire construction of the optical tomographic image obtaining system, which is built into an endoscope. FIG. 2 is a magnified schematic view of an irradiating/light receiving section of the optical tomographic image obtaining system. The optical tomographic image obtaining system obtains and displays a radial optical tomographic image 4 that includes a desired point, specified within an observation portion image 2, which is an image of the interior of a body cavity 1 of a subject displayed on a monitor of the endoscope.

The optical tomographic image obtaining system comprises: an insertion section 10 of the endoscope, which is inserted into a body cavity of a subject; an observation portion image obtaining section, for obtaining the observation portion image 2 of the interior of the body cavity 1; an OCT obtaining section 12, for obtaining an optical tomographic image 4 of a measurement region 3 within the body cavity 1; an OCT probe 13, which is inserted into a forceps channel 71 provided in the insertion portion 10; a display section 14, for displaying the observation portion image 15 and the optical tomographic image 4; a measurement region setting section 15, for setting a measurement region to be measured by a measuring light beam, based on a specified point within the observation portion image 2; and an OCT control section 16, for controlling the optical tomographic image obtaining operations, connected to the OCT obtaining section 12, the OCT probe 13, and the measuring region setting section 15.

The insertion section 10 comprises: a forceps channel 71 that penetrates through the interior thereof; a CCD cable 72 that extends through the interior to the distal end thereof; and a light guide 73 that extends through the interior to the distal end thereof. A CCD imaging element 74 is connected to the distal end of the CCD cable 72. An illumination lens 75 is provided at the distal end of the light guide 73, that is, the distal end of the insertion section 10. AN imaging lens 76 is provided at the distal end of the insertion section 10, and a prism 77 is provided toward the interior of the imaging lens 76.

The light guide 73 is connected to the observation portion image obtaining section 11. The observation image obtaining section 11 is equipped with: a white light source 81, for emitting white light L6; and an image processing section 83, for administering image processes on an image obtained by the CCD imaging element 74, and for outputting a generated image signal to a monitor 192, to be described later.

The OCT obtaining section 12 comprises: a light source 100, for emitting a low coherence light beam L1, of which the central wavelength is 800 nm and the coherence length is 10 μm; an aiming light source 110, for emitting an aiming light beam L2, which is visible light; a fiber coupling optical system 120, for multiplexing the low coherence light beam L1 and the aiming light beam L2, separating the low coherence light beam L1 into a reference light beam L3 and a measuring light beam L4, and multiplexing the reference light beam L3 and the measuring light beam L4; an optical path length changing section 130, which is provided along the optical path of the reference light beam L3, for changing the optical path length thereof; a balance difference detecting section 150, for detecting the light intensity of a coherent light beam L5, which is a light beam created by interference between a measuring light beam L4' reflected at a measurement point within the measurement region 3 and the reference light beam L3; and a signal processing section 160, for performing heterodyne demodulation to determined the intensity of the reflected measuring light beam L4', based on the light intensity of the coherent light beam L5 detected by the balance difference detecting section 150, to generate optical tomographic image data.

The light source 100 of the OCT obtaining section 12 comprises: an SLD 101 (Super Luminescent Diode) for emitting the low coherence light beam L1; and an objective lens 102 for condensing the low coherence light beam L1 emitted from the SLD 101.

The aiming light source 110 comprises: a semiconductor laser 111 for emitting a green laser light beam as the aiming light beam L2; and an objective lens 112 for condensing the aiming light beam L2 emitted from the semiconductor laser 111.

The fiber coupling optical system 120 comprises: a fiber coupler 121, for separating the low coherence light beam L1 into a reference light beam L3 and a measuring light beam L4, and multiplexing the reference light beam L3 and the measuring light beam L4', which is the measuring light beam L4 reflected from the measurement region 3, to obtain the coherent light beam L5; fiber couplers 122 and 123, which are provided between the light source 100 and the fiber coupler 121; a piezoelectric element 124, for generating a slight frequency shift in the reference light beam L3; a fiber 125, for connecting the light source 100 and the fiber coupler 122; a fiber 126, for connecting the aiming light source 110 and the fiber coupler 123; a fiber 127, for connecting the optical path length changing section 130 and the balance difference detecting section 150 via the fiber couplers 121 and 122; and a fiber 128, for connecting the OCT probe 13 and the balance difference detecting section 140 via the fiber coupler 121. Note that the fibers 125, 127, and 128 are single mode optical fibers.

The optical path length changing section 130 comprises: a prism 132; a lens 131, for collimating the reference light beam L3 emitted from the fiber 127, causing the collimated reference light beam L3 to enter the prism 132, and causing the reference light beam L3 reflected by the prism 132 to enter the fiber 127; and a prism moving section 133, for changing the optical path length of the reference light beam L3, by moving the prism 132 in the horizontal direction of FIG. 1. The prism moving section 133 operates under control of the OCT control section 16.

The balance difference detecting section 150 comprises: photodetectors 151 and 152, for measuring the light intensity of the coherent light beam L5; and a differential amplifier 153, for adjusting the input balance of the values detected by the photodetectors 151 and 152 and for amplifying the difference therebetween, after canceling out noise components and drift components.

The OCT probe 13 comprises: a covered tube 173, which is insertable into the forceps channel 71 of the insertion section 10; a fiber 172 that penetrates through the covered tube 173; and an irradiating/light receiving section 174, for irradiating the measuring light beam L4 emitted from the fiber 172 onto the measurement region 3, and for causing the reflected measuring light beam L4' to enter the fiber 172. FIG. 2 is a magnified schematic view of the irradiating/light receiving section 174. The irradiating/light receiving section 174 comprises: an objective lens system 175 capable of changing its focal point distance; a mirror 176, for reflecting the measuring light beam L4 and the reflected measuring light beam L4' perpendicularly, provided more toward the distal end than the objective lens system 174, that is, toward the distal end of the OCT probe 13; a mirror rotating section 184, for rotating the mirror 176 with respect to the covered tube 173; a sheath 177, which is transparent with respect to the measuring light beam L4; and a sheath rotating section 183, for rotating the sheath 177 with respect to the covered tube 173.

The objective lens system 175 comprises: a lens 178, which is fixed to the covered tube 173; and a lens 179, which is fixed to a lens holder 180. The lens holder 180 is tubular in shape. The lens 178 is fixed within the interior of the tubular lens holder 180, and the exterior of the tubular lens holder 180 has threads 181 formed therein. Threads 182 are formed at the interior of the base portion of the sheath 177.

The lens holder 180 is held within the sheath 177, by the threads 181 of the lens holder 180 and the threads 182 of the sheath 177 being in threaded engagement. Note that a rotation preventing mechanism (not shown) is provided on the lens holder 180, and therefore, the lens holder 180 does not rotate with respect to the covered tube 173. For this reason, when the sheath 177 is rotated, the lens holder 180 moves in the direction of the optical axis of the measuring light beam L4, due to the threads 181 and 182. For example, if the sheath rotating section 183 rotates the sheath 177 in the clockwise direction, the lens holder 180 and the lens 179 held therein move from the position indicated by solid lines in FIG. 2, to the position indicated by broken lines. For this reason, the focusing position of the measuring light beam L4 also moves from the position indicated by solid lines to the position indicated by broken lines. Note that the sheath rotating section 183 operates under control of the OCT control section 16.

The mirror rotating section 184 is capable of continuously rotation of the mirror 176, or reciprocal rotation of the mirror 176 within a desired angular range. If the mirror 176 is rotated in a state that the measuring light beam L4 is incident thereon, the irradiation direction of the measuring light beam L4 rotates about the reflection position of the measuring light beam L4 on the mirror 176. Note that the mirror rotating section operates under control of the OCT control section 16.

The mirror 176 and the mirror rotating section 184 function as the irradiation direction rotating means of the present invention. The lens holder 180, the sheath 177, and the sheath rotating section 183 function as the focusing position moving means.

The fiber 172 is built into the covered tube 173 in a fixed state. A probe moving section 185, for rotating and sliding the covered tube 173, is mounted on the base portion of the covered tube. The probe moving section 185 is connected to the measurement region setting section 15, and leads the distal end of the OCT probe 13 to the vicinity of the measurement region 3, which is set by the measurement region setting section 15, by rotating and sliding the covered tube 173.

The display section 14 comprises: a monitor 191, which is an optical tomographic image display means for displaying an optical tomographic image output from the OCT obtaining section 12; a monitor 192, which is an observation portion image display means for displaying the observation portion image 2 output from the observation portion image obtaining section 11; and a pen-type input section 193, which is a position specifying means for specifying a desired pixel position within the observation portion image 2.

The OCT control section 16 is connected to each part of the OCT obtaining section 12, and controls the operation timing of each part as appropriate. In addition, the OCT control section 16 controls the operations of the prism moving section 133, the mirror rotating section 184, and the sheath rotating section 183. Thereby, the irradiation direction of the measuring light beam L4 is rotated, the optical path length of the reference light beam L3 is changed with every rotation of the irradiation direction, to move the position of the measurement point within the measurement region 3 in the direction of the optical axis, and the focusing position of the measuring light beam L4 in the direction of the optical axis with every rotation or every predetermined number of rotations of the irradiation direction.

Next, the operations of the optical tomographic image obtaining system according to the first embodiment of the present invention will be described. An operator inserts the insertion section 10 of the endoscope into a body cavity 1 of a subject, and displays an observation portion image 2 on the monitor 192. At this time, the white light L6 emitted from the white light source 81 of the observation image obtaining section 11 is caused to enter the light guide 73 by the lens 82. After the white light L6 is guided to the distal end of the insertion section 10, it is irradiated on the interior of the body cavity 1 through the illumination lens 75.

Reflected light L7, which is the white light L6 reflected by the body cavity 1, is condensed by the imaging lens 76, is reflected by the prism 77, and is focused on the CCD imaging element 74. An image signal, obtained by photoelectric conversion by the CCD imaging element 74, is output to the image processing section 83 via the CCD cable 72.

The image processing section 83 administers processes, such as correlated double sampling, clamping, blanking, and amplification, to calculate an image signal. The calculated image signal is output to the monitor 192 according to a display timing.

The operator guides the position of the insertion section 10 manually, while viewing the observation portion image 2 displayed on the monitor 192, to guide the insertion section 10 to a desired portion. Thereby, the operator is enabled to view an observation portion image 2 of the desired portion on the monitor 192.

Next, the operations for obtaining the radial optical tomographic image 4 will be described. When obtaining a radial optical tomographic image, the operator inserts the OCT probe 13 into the forceps channel 71 of the insertion section 10 in advance. A point A, at which the optical tomographic image is to be obtained, is specified within the observation portion image 2 by employing the pen-type input section 193, while viewing the observation portion image 2 displayed on the monitor 192.

At this time, the green aiming light beam L2 is emitted from the semiconductor laser 111 of the aiming light source 110. The aiming light beam L2 is condensed by the lens 112, and enters the fiber 126. The aiming light beam L2 is guided via the fiber 126, the fiber coupler 123, the fiber 125, the fiber coupler 122, the fiber 127, the fiber coupler 121, and the fiber 128, and enters the fiber 172 through the lens 171. The aiming light beam L2 is emitted from the fiber 172, condensed by the lenses 178 and 179, reflected by the mirror 176, and is irradiated onto a spot within the body cavity 1 as green light. The reflected light of the aiming light beam L2 is displayed as a bright point within the observation portion image 2 displayed on the monitor 192.

The measurement region setting section 15 calculates the relative positions of the point A, specified within the observation portion image 2, and the bright point, which is the imaged reflection of the aiming light beam L2. Then, the probe moving section 185 rotates and slides the covered tube 173 so that the bright point of the aiming light beam L2 and the specified point A match. A measurement reference point A', for use during obtainment of the radial optical tomographic image, is set within the body cavity 1 by the above operations.

The radial optical tomographic image is an optical tomographic image of a plane, which is perpendicular with respect to the distal end of the OCT probe 13, and that includes the measurement reference point A'.

In order to simplify the description, first, a measurement method for obtaining optical tomographic data of a measurement point within the measurement region, onto which the measuring light beam L4 is irradiated (hereinafter, referred to as "irradiated portion"), will be described. Thereafter, the method for obtaining the radial optical tomographic image will be described.

First, the low coherence light beam L1, of which the central wavelength is 800 nm and the coherence length is 10 μm, is emitted by the SLD 101. The low coherence light beam L1 is condensed by the lens 102, and guided into the fiber 125.

The low coherence light beam L1 passes through the fiber 125, and is guided into the fiber 127 by the fiber coupler 122. Then, the low coherence light beam L1 enters the fiber coupler 121, where it is separated into the reference light beam L3, which propagates through the fiber 127 toward the optical path length changing section 130, and the measuring light beam L4, which propagates through the fiber 128 toward the OCT probe.

The reference light beam L3 is modulated by the piezoelectric element 124, which is provided along its optical path. Thereby, a slight frequency change $\Delta f$ is generated between the reference light beam L3 and the measuring light beam L4.

The measuring light beam L4 is guided from the fiber 128 to the fiber 172 within the OCT probe 13, via the lens 171. The measuring light beam L4 emitted from the fiber 172 is irradiated onto the irradiated portion via the lens 178, the lens 179, and the mirror 176. Note that the lens 179 is moved to a position such that the measuring light beam L4 is focused at the measurement point, by control of the OCT control section 16. The measuring light beam L4', which is reflected at the surface and the interior of the irradiated portion, returns to the fiber 128 via the mirror 176, the lens 179, the lens 178, the fiber 172, and the lens 171. The measuring light beam L4' that returns to the fiber 128 is multiplexed with the reference light beam L3, which returns to the fiber 127, at the fiber coupler 121, as will be described later.

Meanwhile, the reference light beam L3 passes through the fiber 127 and enters the prism 132 via the lens 131 of the optical path length changing section 130, after being modulated by the piezoelectric element 124. After being reflected by the prism 132, the reference light beam L3 passes through the lens 131 again, and returns to the fiber 127. The reference light beam L3 that returns to the fiber 127 is multiplexed with the aforementioned measuring light beam L4' at the fiber coupler 121.

The measuring light beam L4' and the reference light beam L3, which are multiplexed at the fiber coupler 121 become coaxial, and under predetermined conditions, interfere with each other to become coherent light L5 that generates a beat signal.

The reference light beam L3 and the measuring light beam L4' were separated from the low coherence light beam L1, having a short distance in which interference is possible. Therefore, in the case that the optical path length of the measuring light beam L4 (L4') is equal to the optical path length of the reference light beam L3 up to the point where the reference light beam L3 reaches the fiber coupler 121, that is, if the measuring light beam L4' is reflected at the measurement point, the two light beams interfere. The coherent light beam L5 generated by the interference generates a beat signal that waxes and wanes repetitively at the frequency difference $\Delta f$ between the two light beams. Note that the OCT control section 16 controls the prism moving section 133 in advance, such that the optical path lengths of the reference light beam L3 and that of the measuring light beam L4 (L4') reflected at the desired measurement point are equal.

The coherent light beam L5 is separated into two light beams at the fiber coupler 121. One of the two light beams is input to the photodetector 151 of the balance difference detecting section 150 via the fiber 127, and the other light beam is input to the photodetector 152 via the cable 128.

The photodetectors 151 and 152 detect the light intensity of the beat signal from the coherent light beam L5. The difference between the values detected by the photodetector 151 and the photodetector 152 is determined by the differential amplifier 153, and output to the signal processing section 160. Note that the differential amplifier 153 is equipped with a function of adjusting the balance of direct current components input thereto. Therefore, even if drift is present in the low coherence light beam L1 emitted from the light source 100, the drift component is canceled out, by the difference being amplified after the balance of direct current components are adjusted. Thereby, only the beat signal component is detected.

Tomographic data regarding a predetermined depth of the irradiated portion within the body cavity 1 is obtained by the operations described above.

Figure 3:
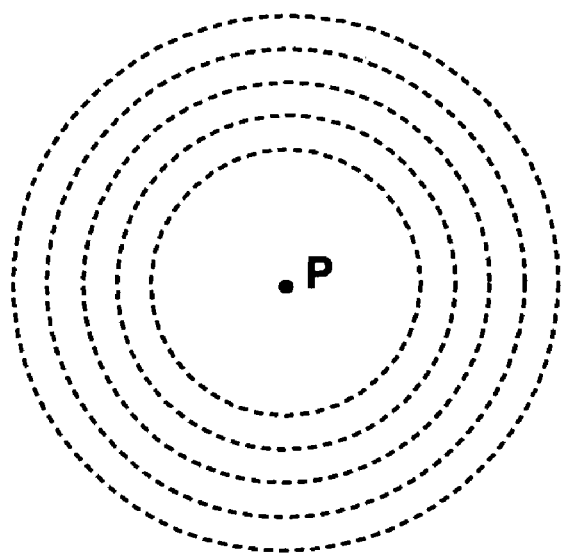
FIG. 3 is a diagram for explaining measurement points and focusing positions.

The operations as described above are repeated, while rotating the irradiation direction of the measuring light beam L4. Beat signal components are detected every time that the position of the measurement point, which is perpendicular to the direction of the optical axis, moves approximately 5 μm. Thereby, data regarding measurement points, which are equidistant from the rotational center P of the irradiation direction of the measuring light beam L4, that is, the mirror 176, within the measurement region 3 can be obtained, as illustrated in FIG. 3.

The OCT control section 16 controls the mirror rotating section 183 to rotate the irradiation direction of the measuring light beam L4 one full rotation. Then, the OCT control section 16 controls the prism moving section 133 of the optical path length changing section 130 to increase the optical path length of the reference light beam L3 by 5 μm. Simultaneously, the sheath rotating section 183 is controlled to cause the focusing position of the measuring light beam L4 5 μm further in the direction of the optical axis thereof. In this state, data regarding measurement points are obtained at 5 μm intervals again, while rotating the irradiation direction of the measuring light beam L4. Thereby, data regarding measurement points, which are 5 μm toward the exterior from the first measurement points, are obtained. By obtaining data regarding measurement points over 400 rotations in the manner described above, data regarding measurement points within an annular region having a ring width of 2 mm can be obtained along the measurement region 3.

The signal processing section 160 performs heterodyne demodulation to derive the intensity of the measuring light beam L4', which is reflected at predetermined surfaces of each measurement point, from the light intensity of the coherent light beam L5 detected by the balance difference detecting section 150. The intensities of the measuring light beam L4' are converted to a radial optical tomographic image, and output to the monitor 191.

The monitor 191 displays the radial optical tomographic image 4 output by the signal processing section 160. The radial optical tomographic image 4, which is an annular cross section of the body cavity 1 as illustrated in FIG. 1, is displayed by the operations described above.

As is clear from the description above, the focusing position in the direction of the optical axis of the measuring light beam L4 is moved to match rotation of the irradiation direction thereof. Therefore, the movement speed of the focusing position can be reduced compared to conventional apparatuses. Accordingly, the necessity of a conventional large focusing position moving means, which is capable of high speed movement, is obviated, and the optical tomographic image obtaining system, capable of obtaining optical tomographic images at high resolution, can be miniaturized.

The focusing position moving means, constituted by the lens holder 180, the sheath 177, and the sheath rotating section 183, is miniaturized. Therefore, it is possible to provide these elements in the distal end of the OCT probe 13. Accordingly, the optical tomographic image obtaining apparatus of the present invention can easily be built into an endoscope, which improves the utility thereof.

The wavelength of the measuring light beam L4 is 800 nm. Therefore, transmittance with respect to living tissue is high, and reliable optical tomographic images can be obtained.

Note that in the case that an optical tomographic image of a narrow region within the body cavity 1 is desired, it is not necessary to rotate the measuring light beam L4 360 degrees. Reciprocal rotation may be performed within a desired angular range, and an optical tomographic image within the narrow region may be obtained. In this case, the measurement time required to obtain the optical tomographic image can be reduced.

In the embodiment described above, the position of the measurement point in the direction of the optical axis was moved for every rotation of the irradiation direction. Alternatively, the position of the measurement point can be moved continuously, synchronous with the rotation.

In the embodiment described above, the movement of the focusing position in the direction of the optical axis was performed after each single rotation of the irradiation direction. Alternatively, the movement of the focusing position may be performed after every predetermined number of rotations of the irradiation direction. Note that in this case as well, it is preferable to move the focal point position of the objective lens system before the distance that the measurement point is moved along the direction of the optical axis exceeds the focal depth of the objective lens system.

Figure 4:
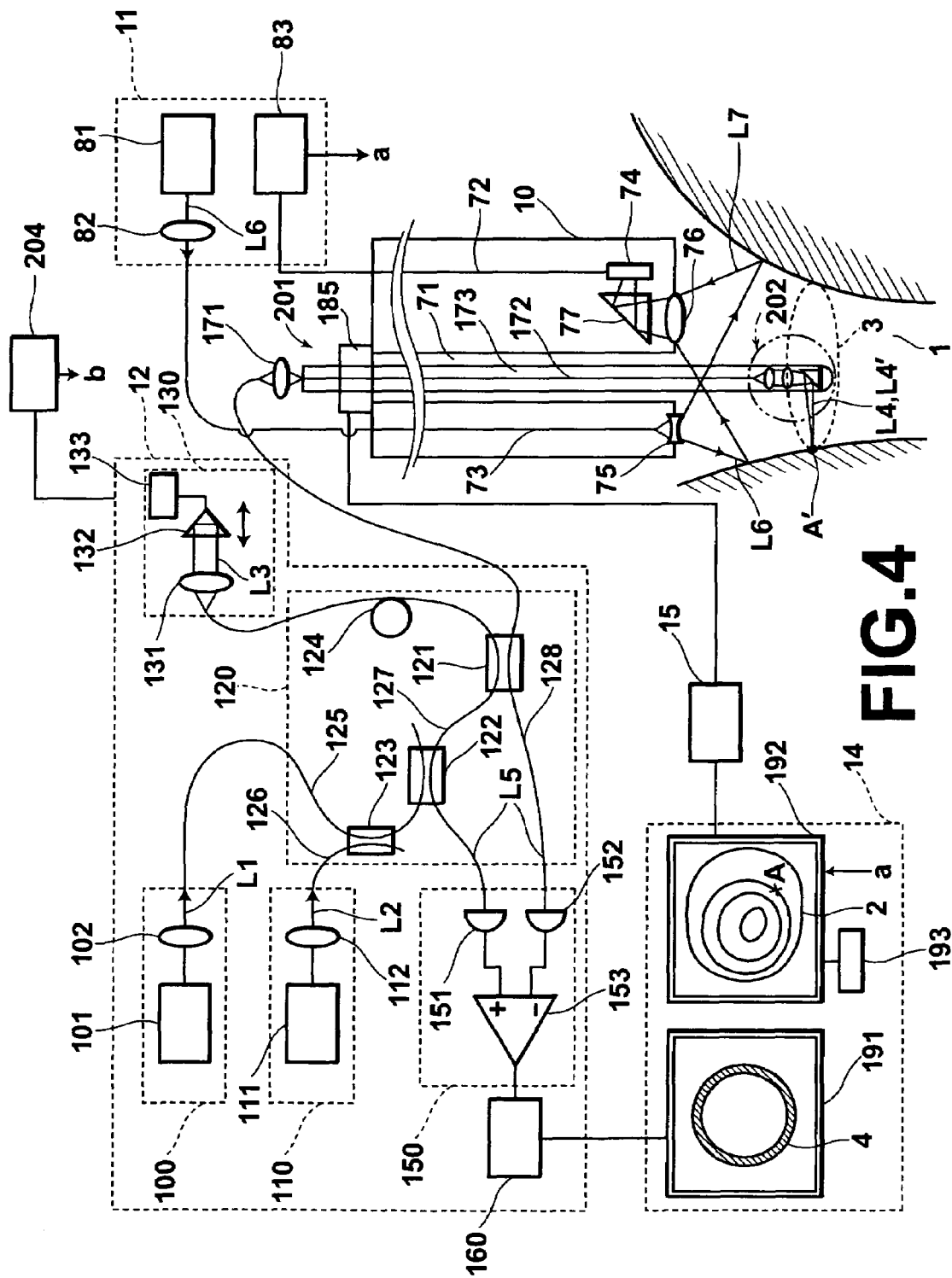
FIG. 4 is a schematic view illustrating the entire construction of an optical tomographic image obtaining system according to a second embodiment of the present invention.
Figure 5:
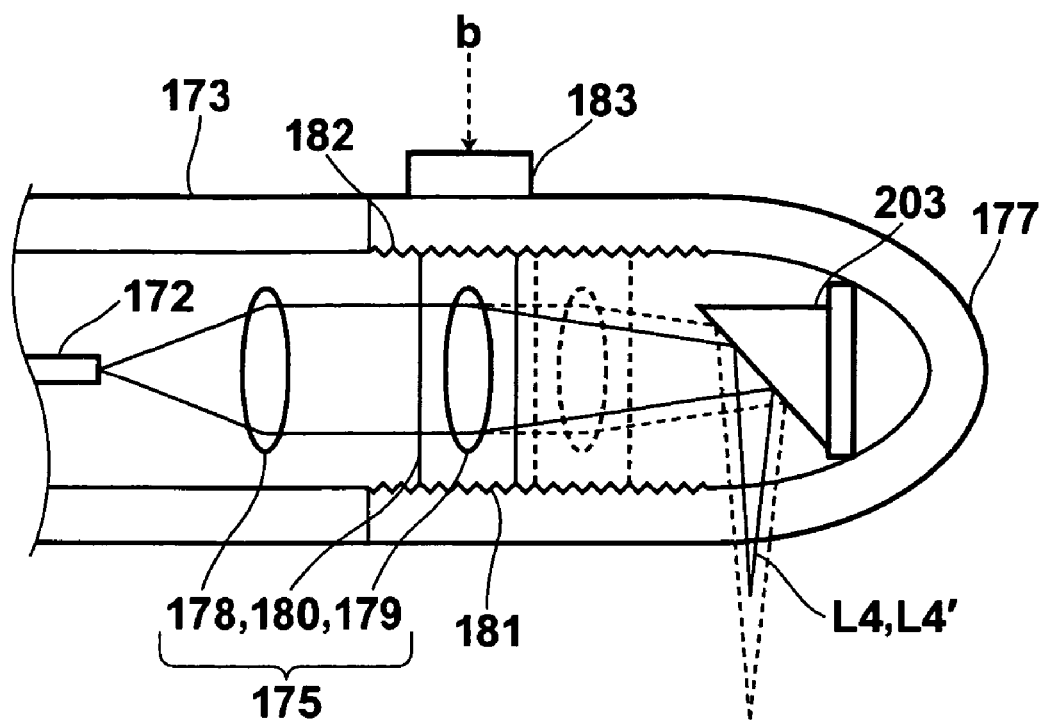
FIG. 5 is a magnified schematic view of an irradiating/light receiving section of the optical tomographic image obtaining system of FIG. 4.

Next, an optical tomographic image obtaining system according to a second embodiment of the present invention will be described with reference to FIG. 4 and FIG. 5. FIG. 4 is a schematic view illustrating the entire construction of the optical tomographic image obtaining system, which is built into an endoscope. FIG. 5 is a magnified schematic view of an irradiating/light receiving section of the optical tomographic image obtaining system. In FIG. 4, elements which are the same as those illustrated in FIG. 1 are labeled with the same reference numerals, and in FIG. 5, elements which are the same as those illustrated in FIG. 2 are labeled with the same reference numerals. Detailed descriptions regarding the parts which are in common between the first and second embodiments will be omitted, unless particularly necessary.

An OCT probe 201 comprises: the covered tube 173, which is insertable into the forceps channel 71 of the insertion section 10; the fiber 172 that penetrates through the covered tube 173; and an irradiating/light receiving section 202, for irradiating the measuring light beam L4 emitted from the fiber 172 onto the measurement region 3, and for causing the reflected measuring light beam L4' to enter the fiber 172. FIG. 5 is a magnified schematic view of the irradiating/light receiving section 202. The irradiating/light receiving section 202 comprises: the objective lens system 175; the sheath 177; the sheath rotating section 183; and a mirror 203, for reflecting the measuring light beam L4 and the reflected measuring light beam L4' perpendicularly, fixed to the distal end of the sheath 177.

That is, in the second embodiment, rotation of the irradiation direction of the measuring light beam L4 and movement of the focusing position of the measuring light beam L4 are performed simultaneously, by the sheath rotating section 183 rotating the sheath 177. Note that the threads 182 of the sheath 177 and the threads 181 of the lens holder 180 are formed such that the focusing position of the measuring light beam L4 moves 5 μm with every single rotation of the irradiation direction thereof.

An OCT control section 204 is connected to each part of the OCT obtaining section 12, and controls the operation timing of each part as appropriate. In addition, the OCT control section 16 controls the operations of the sheath rotating section 183. Thereby, the irradiation direction of the measuring light beam L4 is rotated, and the focusing position of the measuring light beam L4 in the direction of the optical axis thereof is moved such that it substantially matches the measuring point as a linked operation. Further, the prism moving section 133 of the optical path length changing section 130 is controlled to change the optical path length of the reference light beam L3, thereby moving the position of the measurement point in the direction of the optical axis thereof within the measurement region 3, as a linked operation.

Note that the mirror 203, the sheath 177, and the sheath rotating section 183 function as the irradiation direction rotating means of the present invention. The lens holder 180, the sheath 177, and the sheath rotating section 183 function as the focusing position moving means.

When obtaining an optical tomographic image, the irradiation direction of the measuring light beam L4 is rotated. Simultaneously, the focusing position of the measuring light beam L4 is moved continuously. During the course of a single rotation of the irradiation direction of the measuring light beam L4, the focusing position moves 5 μm in the direction of the optical axis thereof. In addition, the OCT control section 204 controls the prism moving section 133 of the optical path length changing means 130 to continuously change the optical path length of the reference light beam L3 as a linked operation with the rotation of the irradiation direction. The length of the optical path of the reference light beam L3 is increased by 5 μm during the course of a single rotation of the irradiation direction of the measuring light beam L4.

Figure 6:
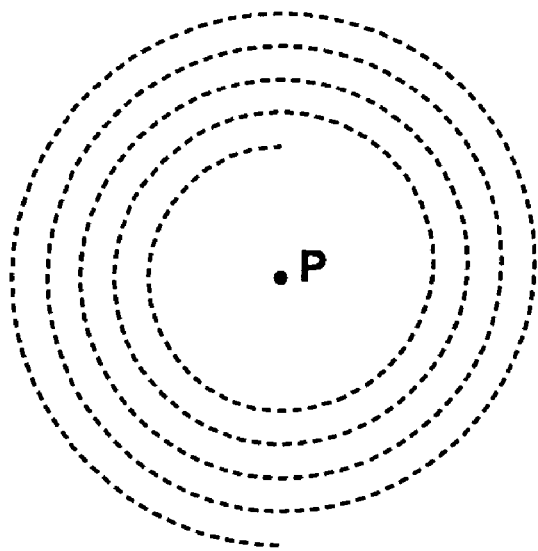
FIG. 6 is a diagram for explaining measurement points and focusing positions.

Beat signal components are detected every time that the irradiation position of measuring light beam L4 moves approximately 5 μm in the direction of rotation. Thereby, data regarding measurement points, which extend outward in a spiral from the rotational center P of the irradiation direction of the measuring light beam L4, that is, the mirror 203, within the measurement region 3 can be obtained, as illustrated in FIG. 6. By rotating the irradiation direction of the measuring light beam L4 400 times, optical tomographic image data regarding an annular region having a ring width of 2 mm can be obtained.

As is clear from the description above, the measurement depth, that is, the position of the measurement point in the direction of the optical axis, is moved continuously, synchronous with the rotation of the irradiation direction of the measuring light beam L4. At the same time, the focusing position of the measuring light beam L4 in the direction of the optical axis thereof is moved continuously. Therefore, the movement speed of the focusing position can be reduced compared to conventional apparatuses. Accordingly, the necessity of a conventional large focusing position moving means, which is capable of high speed movement, is obviated, and the optical tomographic image obtaining system, capable of obtaining optical tomographic images at high resolution, can be miniaturized. Further, by causing the irradiation direction rotating means and the focusing position moving means to operate in a linked manner, the time required to move the focusing position after each rotation is eliminated. Thereby, the optical tomographic image can be obtained at even higher speed. In addition, if the irradiation direction rotating means and the focusing position moving means are mechanically linked so as to operate in a linked manner, these means can be realized with a simple construction, and they can be further miniaturized.

Note that in the embodiments described above, descriptions have been given for cases in which a single optical tomographic image is obtained. Alternatively, a plurality of optical tomographic images may be obtained while sliding the position of the OCT probe in the vertical direction of FIG. 1, to obtain three dimensional optical tomographic images.

What is claimed is:

1. An optical tomographic image obtaining apparatus that divides a low coherent light beam, having a coherence length of 20 μm or less, into a measuring light beam and a reference light beam; changes the optical path length of at least one of the reference light beam and the measuring light beam; irradiates the measuring light beam onto a target of measurement; receives the measuring light beam, which is reflected from the target of measurement; causes the reflected measuring light beam and the reference light beam to interfere; and measures the light intensity of the coherent light after the interference, to obtain optical tomographic images of the target of measurement, comprising:

irradiation direction rotating means, for causing the irradiation direction of the measuring light beam to rotate about a single point;

optical path length changing means, for changing the optical path length of at least one of the reference light beam and the measuring light beam, synchronous with the rotation of the irradiation direction of the measuring light beam;

an objective lens system, for focusing the measuring light beam; and focusing position moving means, for moving the focusing position in the direction of the optical axis of the measuring light beam, by moving the focal point of the objective lens system, synchronous with the rotation of the irradiation direction of the measuring light beam.

2. An optical tomographic image obtaining apparatus as defined in claim 1, wherein:

the irradiation direction rotating means rotates the irradiation direction of the measuring light beam unidirectionally;

the optical path length changing means continuously changes the optical path length, synchronous with the rotation; and the focusing position moving means continually moves the focusing position, synchronous with the rotation.

3. An optical tomographic image obtaining apparatus as defined in claim 2, wherein:

the irradiation direction rotating means, the objective lens system, and the focusing position moving means are provided at the distal end of a probe, which is insertable into a forceps channel of an endoscope.

4. An optical tomographic image obtaining apparatus as defined in claim 3, wherein:

the target of measurement is a portion of a living organism; and the wavelength of the low coherent light beam is within a range of 600 nm to 1700 nm.

5. An optical tomographic image obtaining apparatus as defined in claim 2, wherein:

the target of measurement is a portion of a living organism; and the wavelength of the Low coherent light beam is within a range of 600 nm to 1700 nm.

6. An optical tomographic image obtaining apparatus as defined in claim 1, wherein:

the irradiation direction rotating means, the objective lens system, and the focusing position moving means are provided at the distal end of a probe, which is insertable into a forceps channel of an endoscope.

7. An optical tomographic image obtaining apparatus as defined in claim 6, wherein:

the target of measurement is a portion of a living organism; and the wavelength of the low coherent light beam is within a range of 600 nm to 1700 nm.

8. An optical tomographic image obtaining apparatus as defined in claim 1, wherein:

the target of measurement is a portion of a living organism; and the wavelength of the low coherent light beam is within a range of 600 nm to 1700 nm.

9. An optical tomographic image obtaining apparatus of claim 1, wherein:

the optical axis of the measuring light beam rotating about a single point, is at an angle with the axis of the objective lens system.

10. An optical tomographic image obtaining apparatus of claim 9, wherein:

said angle is greater than zero degrees.

11. An optical tomographic image obtaining apparatus of claim 10, wherein:
the movement of the focusing point in the direction of the optical axis of the measuring beam light is performed after every predetermined number of rotations of the measuring light beam about a single point.

12. An optical tomographic image obtaining apparatus of claim 10, wherein:
the movement of the focusing point in the direction of the optical axis of the measuring beam light is performed continuously with the rotation of the measuring light beam about a single point.

13. An optical tomographic image obtaining apparatus of claim 1, wherein:
the focal point of the objective lens system is independent of the position of the irradiation direction rotation means.

14. An optical tomographic image obtaining apparatus of claim 1, wherein:
the movement of the focusing point in the direction of the optical axis of the measuring beam light is performed after every predetermined number of rotations of the measuring light beam about a single point.

15. An optical tomographic image obtaining apparatus of claims 1, wherein:
the movement of the focusing point in the direction of the optical axis of the measuring beam light is performed continuously with the rotation of the measuring light beam about a single point.

* * * * *